United States Patent [19]

Knodel et al.

[11] Patent Number: 5,769,303
[45] Date of Patent: Jun. 23, 1998

[54] ENDOSCOPIC SURGICAL STAPLER WITH COMPACT PROFILE

[75] Inventors: Tim Knodel; Bryan D. Knodel, both of Cincinnati; Anil Nalagatla, West Carrollton; Dale R. Schulze, Lebanon, all of Ohio

[73] Assignee: Ethicon Endo-Surgery, Inc., Cincinnati, Ohio

[21] Appl. No.: 842,254

[22] Filed: Apr. 24, 1997

Related U.S. Application Data

[62] Division of Ser. No. 545,297, Oct. 19, 1995, Pat. No. 5,697,542.

[51] Int. Cl.⁶ .................................................. A61B 17/068
[52] U.S. Cl. ...................... 227/176.1; 227/19; 227/178.1
[58] Field of Search .................................. 227/19, 175.1, 227/176.1, 178.1, 179.1, 180.1

[56] References Cited

U.S. PATENT DOCUMENTS

| | | | |
|---|---|---|---|
| 3,269,631 | 8/1966 | Takara ........................................ | 227/19 |
| 4,169,476 | 10/1979 | Hiltebrandt .............................. | 128/325 |
| 4,198,982 | 4/1980 | Fortner et al. ............................ | 227/19 |
| 4,505,272 | 3/1985 | Utyamyshev et al. .................. | 128/305 |
| 4,784,137 | 11/1988 | Kulik et al. .............................. | 128/334 |
| 5,040,715 | 8/1991 | Green et al. .......................... | 227/176.1 |
| 5,071,430 | 12/1991 | de Salis et al. .......................... | 606/219 |
| 5,170,925 | 12/1992 | Madden et al. ....................... | 227/175.1 |
| 5,307,976 | 5/1994 | Olson et al. .......................... | 227/178.1 |
| 5,425,745 | 6/1995 | Green et al. ............................. | 606/219 |

FOREIGN PATENT DOCUMENTS

| | | |
|---|---|---|
| 51-149985 | 5/1950 | Japan . |
| 728848 | 5/1980 | Russian Federation . |

*Primary Examiner*—Scott A. Smith
*Attorney, Agent, or Firm*—Matthew S. Goodwin

[57] ABSTRACT

A surgical stapler having an end effector with a reduced stacking height for its components to decrease the diameter of a trocar cannula or other access device during minimally invasive surgery is disclosed. The end effector includes an elongated channel containing a staple cartridge and an anvil movable toward and away from the channel. The anvil is movable to first, second and third fixed positions relative to the channel. The first fixed position is a closed position which eliminates clearance between the anvil and cartridge. The second fixed position is an open position for inserting tissue between the anvil and cartridge. The third fixed position is a clamped position where a tissue-clamping gap exists between the anvil and cartridge to properly clamp tissue. The elimination of clearance between the anvil and cartridge of the first fixed position of the anvil reduces the stacking height, and therefore enables the user to insert the stapler through a smaller diameter access opening.

2 Claims, 8 Drawing Sheets

ENDOSCOPIC SURGICAL STAPLER WITH COMPACT PROFILE

This is a division, of application Ser. No. 08/545,297 filed Oct. 19, 1995, now U.S. Pat. No. 5,697,542, which is hereby incorporated by reference.

BACKGROUND OF THE INVENTION

This invention relates to surgical instruments for performing endoscopic procedures. More particularly, it relates to endoscopic surgical staplers which have a compact configuration particularly adapted for minimally invasive surgical procedures.

During an endoscopic surgical procedure, access to the surgical site within the body cavity is provided through openings of a small diameter made in the body wall. An instrument frequently used to provide this access is the trocar. The trocar is an assembly which includes an obturator and a cannula. The obturator has a sharp tip which is used to puncture the body wall to provide the access opening. The obturator slides within the cannula, which is a hollow, cylindrical sleeve. When the obturator has punctured the body wall, the obturator is removed from the cannula The cannula, however, remains in place within the opening made in the body wall by the obturator. Consequently, the cannula provides a cylindrical passageway to gain access to the surgical site within the body cavity.

Accordingly, a characteristic feature of many endoscopic surgical instruments is a long cylindrical shaft which can slide through the trocar cannula. At the business end of the shaft, which is the end of the instrument coming into contact with tissue at the surgical site within the body cavity, an "end effector" is provided to manipulate the tissue in some way to carry out a desired surgical procedure. The business end, including the end effector, must likewise be capable of sliding through the trocar cannula.

In most cases, it is the end effector which dictates the size of the cylindrical shaft. The cylindrical shaft is typically sized to have a cross-sectional diameter large enough to house the combination of components of the end effector.

One particularly desired function of an end effector of an endoscopic surgical instrument is the ability of the end effector to fire staples into bodily tissue for fastening the tissue. In some procedures, it is desirable to first clamp the tissue so that the clamped tissue may be fastened when staples are fired into and through the tissue. Instruments with end effectors which fire staples into clamped tissue are referred as linear staplers and cutters (cutters are so named because they simultaneously cut the tissue with a knife between rows of fired staples).

The end effector of a linear stapler or cutter typically has two opposed, elongated jaws. The jaws have internal tissue-contacting surfaces between which the tissue is clamped. The jaws are often described as a lower jaw and an upper jaw. The lower and upper jaws move relative to each other. When the jaws are moved to an open position, the tissue-clamping surfaces of the jaws are spaced from each other so that tissue can be placed between the two surfaces. When the jaws are moved to their closed position, the tissue-contacting surfaces of the jaws are positioned adjacent each other so that the tissue placed between the jaws is clamped.

Linear cutters and staplers have conventionally had a fixed lower jaw and a pivoting upper jaw which pivots from an open to a closed position relative to the lower jaw. The fixed lower jaw may include a channel for receiving a staple cartridge. The upper jaw typically includes an anvil. Accordingly, when a linear stapler or cutter is used, tissue is placed between the tissue and anvil. When the upper jaw is placed in the open position, the upper jaw is pivoted to its closed position to clamp tissue between the cartridge and anvil, and staples are subsequently fired from the cartridge into the clamped tissue for formation against the anvil.

Since the cylindrical shaft of an endoscopic linear stapler or cutter must be sized to house the components of the end effector, it is the end effector which therefore dictates the size of the endoscopic portion of the instrument. Therefore, the end effector also controls the size of the trocar which is used to provide access to the surgical site within the body cavity. Accordingly, it has always been a desired goal of engineers and designers in the field of endoscopic surgical instrumentation to effectively reduce the overall size of the end effector to in turn minimize the size of the trocar which is needed to provide access into the body.

The overall "size" of the end effector of a linear stapler or cutter is governed by the number of components which make up the end effector and the clearances which are necessary between the components. The critical size parameters which dictate the diameter of the cylindrical shaft of the instrument are the stacking height of each of the components of the end effector and the extent to which the components must be spaced from each other. Obviously, the overall size of the end effector can be reduced if the components of the end effector can be tightly "sandwiched" together to minimize the stacking height.

In connection with the endoscopic stapler or cutter, the stacked components of the end effector include the lower and upper jaws, and the staple cartridge received within the lower jaw. In addition, a clearance has conventionally been provided between the lower and upper jaws to account for the ability to place tissue between the jaws for clamping. It is these stacked components and the clearance between the upper and lower jaws which in turn define the size of the cylindrical shaft of the instrument. While the size of the cylindrical shaft and therefore the endoscopic portion of linear staplers and cutters has been acceptable, there has been and will continue to be a push for effectively smaller instruments.

Accordingly, the surgical community would benefit from a change in the design of the end effector of an endoscopic surgical stapler which would reduce the stacking height of the end effector. Such a reduction in the stacking height would enable the use of an instrument with an endoscopic portion having a cylindrical shaft of a diameter smaller than that which has been previously been used or described in the literature. In this way, the size of the trocar providing access to the endoscopic surgical site can likewise be reduced. Ultimately, the endoscopic procedure can indeed become more minimally invasive because the size of the openings made through the body wall can be reduced.

SUMMARY OF THE INVENTION

The invention is an endoscopic surgical stapler which is capable of clamping bodily tissue prior to firing staples to fasten the tissue. The stapler comprises an end effector which includes an anvil and an elongated channel. The channel contains a staple cartridge. The anvil faces the channel, and it is movable toward and away from the channel.

The anvil is movable to first, second and third fixed positions relative to the channel. The first fixed position is a closed position in which the anvil is in intimate contact with the staple cartridge. This contacting position eliminates any clearance between the anvil and cartridge. The second fixed position is an open position in which the anvil is spaced from the cartridge for subsequent clamping. In the open position, bodily tissue can be inserted between the anvil and cartridge for subsequent clamping. The third fixed position is a clamped position in which the anvil is adjacent the cartridge. In the clamped position, there is a tissue-clamping gap between the anvil and cartridge to enable the bodily tissue to be properly clamped between the anvil and cartridge.

Significantly, the existence of the first fixed position of the anvil on the end effector of the surgical stapler of this invention provides for the lowest stacking height obtainable for a stapler which contains a cartridge-filled channel and an opposed, movable anvil. The stacking height is optimized because the clearance conventionally associated with the tissue gap between the anvil and cartridge has been eliminated. Accordingly, it becomes possible to insert the stapler through a trocar cannula having a smaller diameter because the stacking height of the end effector of the stapler has been optimized. Of course, this attendant benefit of the stapler is a highly desirable attribute for instrumentation designed for minimally invasive surgical applications.

During a minimally invasive surgical procedure, where access to the surgical site is provided through tubular cannulas of small diameter, the stapler of this invention is initially adjusted so that the anvil on the end effector is moved to its first fixed position relative to the channel. Since the clearance between the anvil and cartridge is eliminated to lessen the stacking height of the end effector, a cannula having a diameter smaller than that of a conventional cannula can be used to provide access to the site. With the anvil in its first fixed position, the end effector is inserted through the cannula and positioned adjacent the bodily tissue to be clamped. Once properly positioned, the end effector is adjusted to move the anvil from the first to second fixed positions relative to the channel. In the second fixed position, the anvil is spaced from the cartridge, and the bodily tissue can be readily inserted between the cartridge and anvil. When the tissue is inserted, the end effector is again adjusted to move the anvil from its second to third fixed positions. In its third fixed position, the anvil has moved to a position adjacent the cartridge, and the tissue is clamped between the cartridge and anvil with a clinically acceptable tissue-clamping gap between the cartridge and anvil. At this point, the staples can then be fired from the cartridge for formation on the anvil to fasten the clamped tissue. Once the staples have been fired, the anvil is moved from its third to second fixed positions to remove the end effector from the fastened tissue. The anvil is then moved to the first fixed position so that the end effector can be readily withdrawn from the trocar cannula.

The endoscopic surgical stapler of this invention can be used during any minimally invasive surgical applications, especially those where it is desired to further minimize trauma to the patient by continuing to reduce the diameter of trocar cannulas and other access devices.

DETAILED DESCRIPTION OF THE PREFERRED EMBODIMENT

Figure 1:
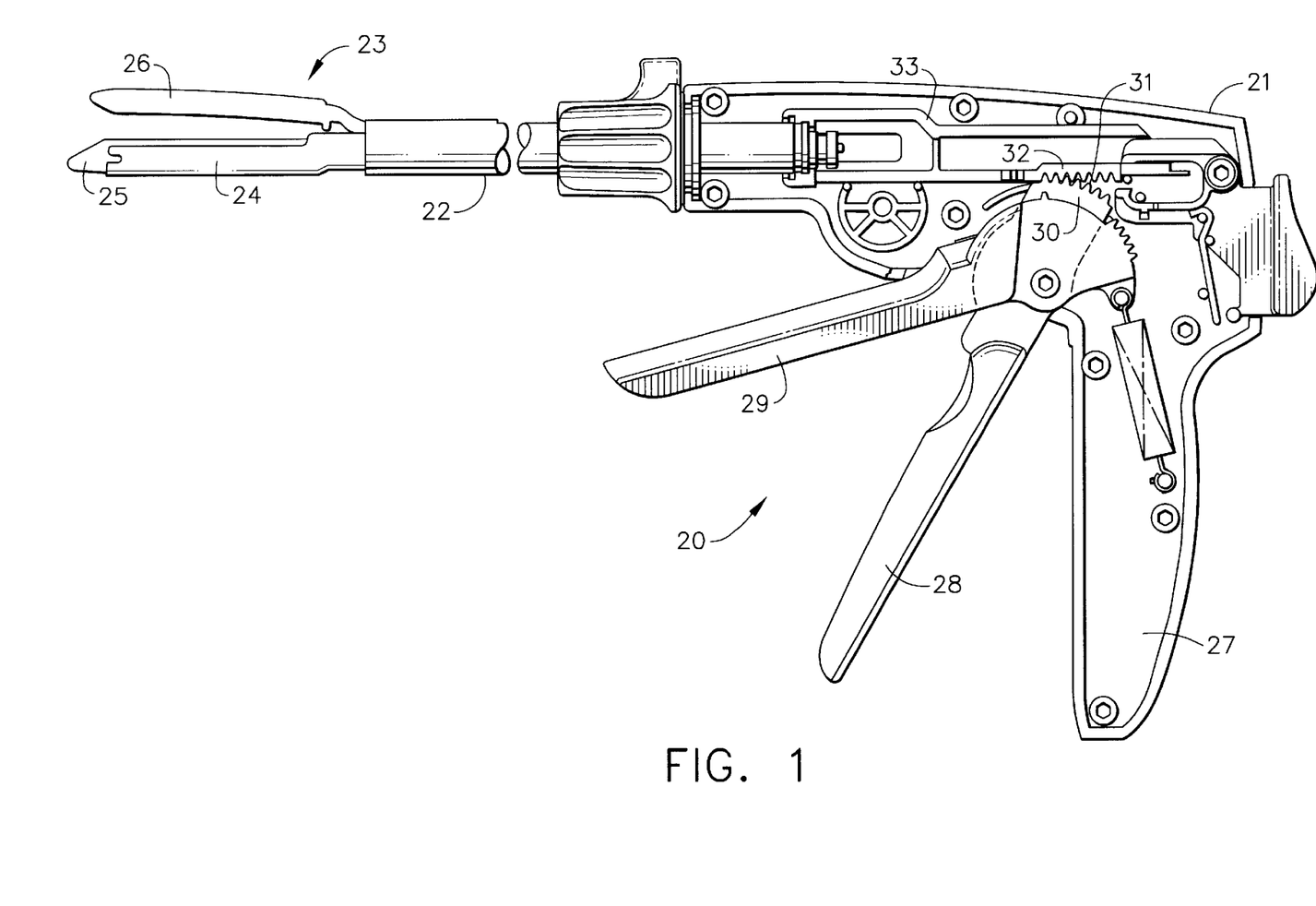
FIG. 1 is a side elevation of an endoscopic linear cutter of this invention, with one half of the frame subassembly removed to expose interior components.

Referring to FIG. 1, a surgical stapler 20 which is capable of practicing the unique benefits of this invention is illustrated. The stapler has a frame 21 (the frame is a subassembly consisting of bottom and top halves, and the top half has been removed to depict the components housed inside the frame), a closure sleeve 22 extending from the frame, and an end effector 23 extending from the distal end of the closure sleeve. The end effector includes an elongated channel 24 for receiving a staple cartridge 25. It also includes a movable anvil 26 facing the cartridge upon which the staples from the cartridge are formed.

The frame 21 has a palm grip handle 27 and clamping and firing triggers 28 and 29, respectively, pivotally mounted to the frame. The stapler is shown in FIG. 1 with the anvil spaced from the cartridge. Bodily tissue (not shown) can be inserted between the cartridge and anvil. The user grips the frame with the palm grip handle and squeezes the clamping trigger against the palm grip handle. In so doing, a pinion 30 with a set of gear teeth 31 drives a gear rack 32 forwardly. The gear rack is attached to an actuator 33, and the actuator is fixed to the closure sleeve 22. Consequently, the closure tube moves from rearward to forward positions, and causes the anvil to move from its position spaced from the cartridge to a clamping position. When the clamping trigger is fully actuated and the bodily tissue is clamped, the firing trigger can then be squeezed to fire the staples against the anvil to fasten the tissue. A more detailed description of the components of the frame and their interaction with the clamping and firing mechanisms of an endoscopic linear cutter are described in commonly assigned, copending application Ser. No. 08/191,142, filed Mar. 18, 1994.

Figure 2:
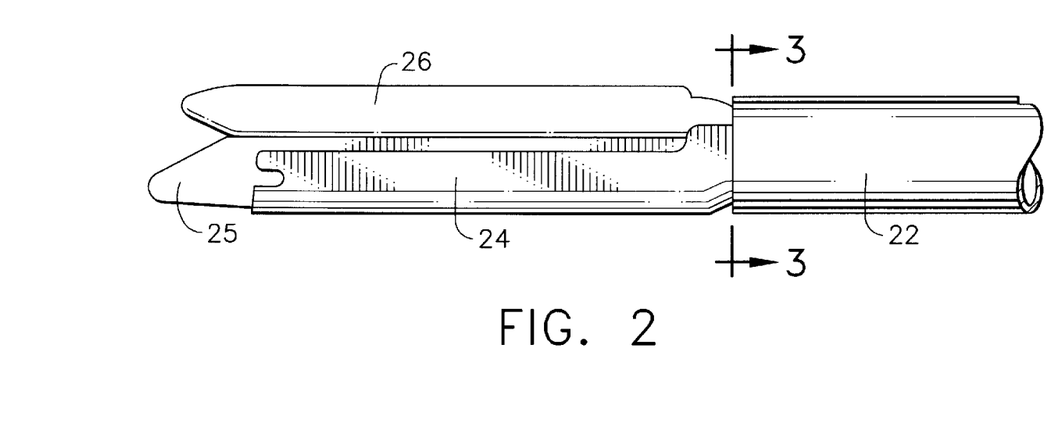
FIG. 2 is the end effector of FIG. 1 where the anvil is in its first fixed position relative to the channel.
Figure 3:
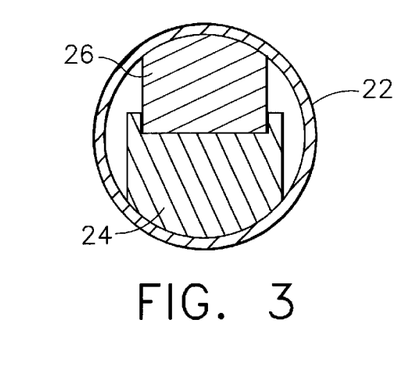
FIG. 3 is a section generally taken along line 3—3 of FIG. 2.

Referring to FIGS. 2 and 3, the minimum stacking height of the end effector is illustrated. The anvil 26 lies flush against the cartridge 25, and there is no gap between the anvil and cartridge. The diameter of the sleeve can therefore be sized to snugly fit the elongated channel and anvil, and it is unnecessary to increase the diameter to allow for the conventional gap between the anvil and cartridge for tissue-clamping.

Figure 4:
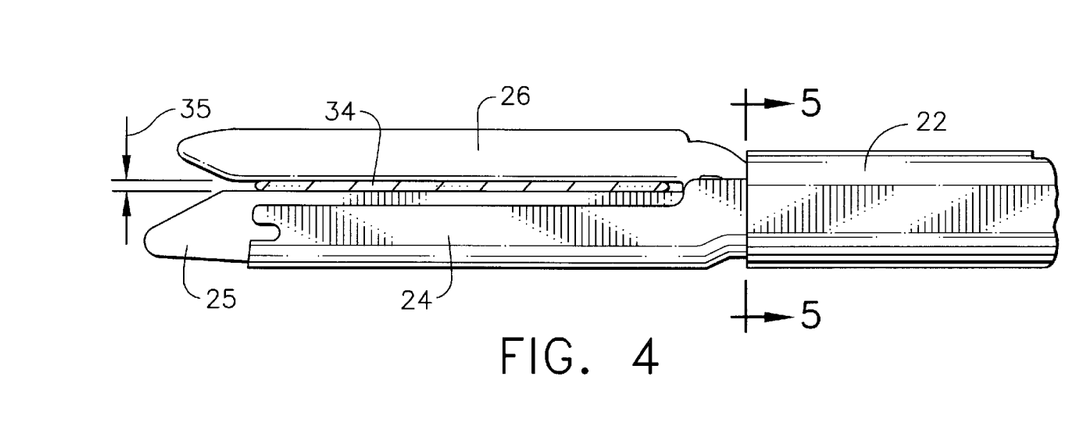
FIG. 4 is a partial side elevation view of the end effector where the anvil is in its third fixed position relative to the channel.
Figure 5:
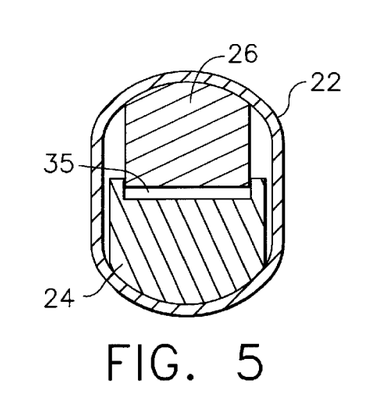
FIG. 5 is a section generally taken along line 5—5 of FIG. 4.

Referring to FIGS. 4 and 5, bodily tissue 34 has been inserted between the anvil and staple cartridge. The anvil is positioned adjacent the cartridge, and a tissue-clamping gap is displayed between the anvil and cartridge. In order for the sleeve to accommodate the clearance necessitated by the tissue-clamping gap, the distal end of the sleeve is made to be expandable so that it will deform to appropriately accommodate the stacking height of the end effector components, including the conventional tissue-clamping gap 35. The sleeve can be made of a thin-walled, metal tube or a polymer which elongates into a non-circular shape to accommodate the increased height of the end-effector.

Figure 6:
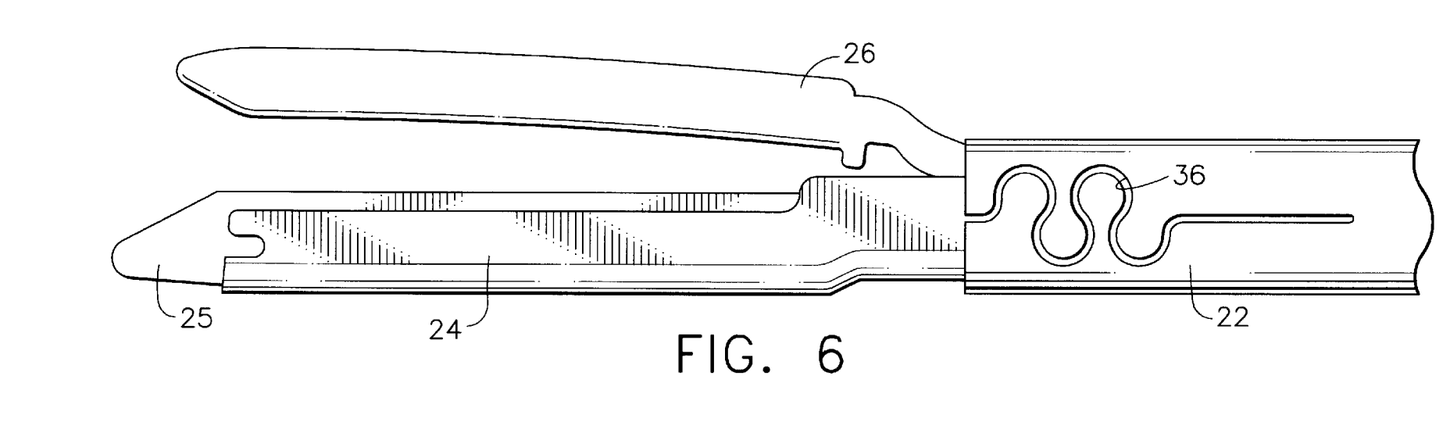
FIG. 6 is a fragmentary side elevation view of an alternative embodiment of the end effector.
Figure 7:
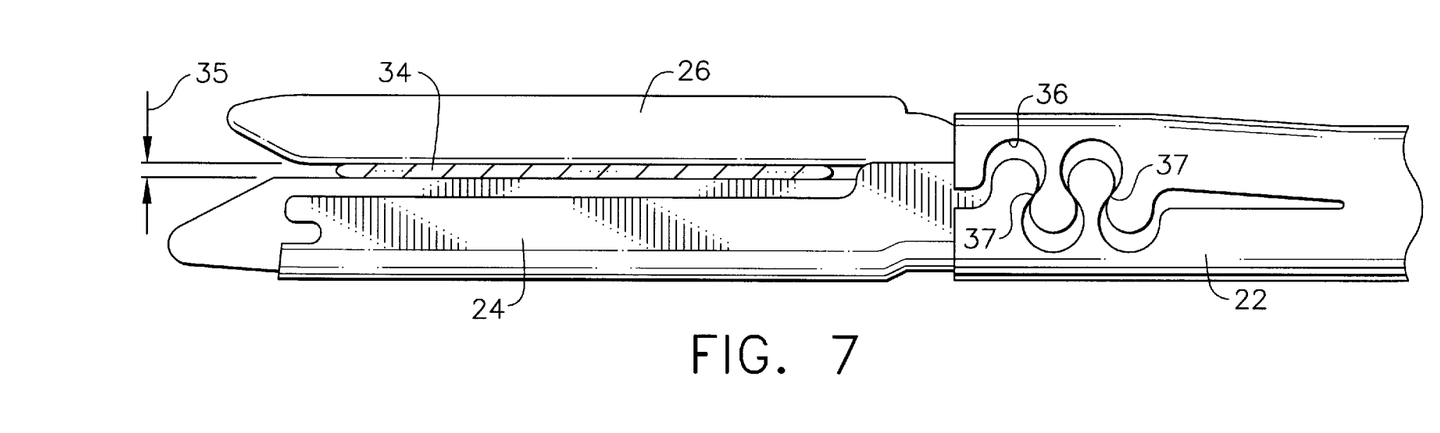
FIG. 7 is a fragmentary side elevation view of the embodiment of the end effector illustrated in FIG. 6 clamped on tissue.
Figure 8:
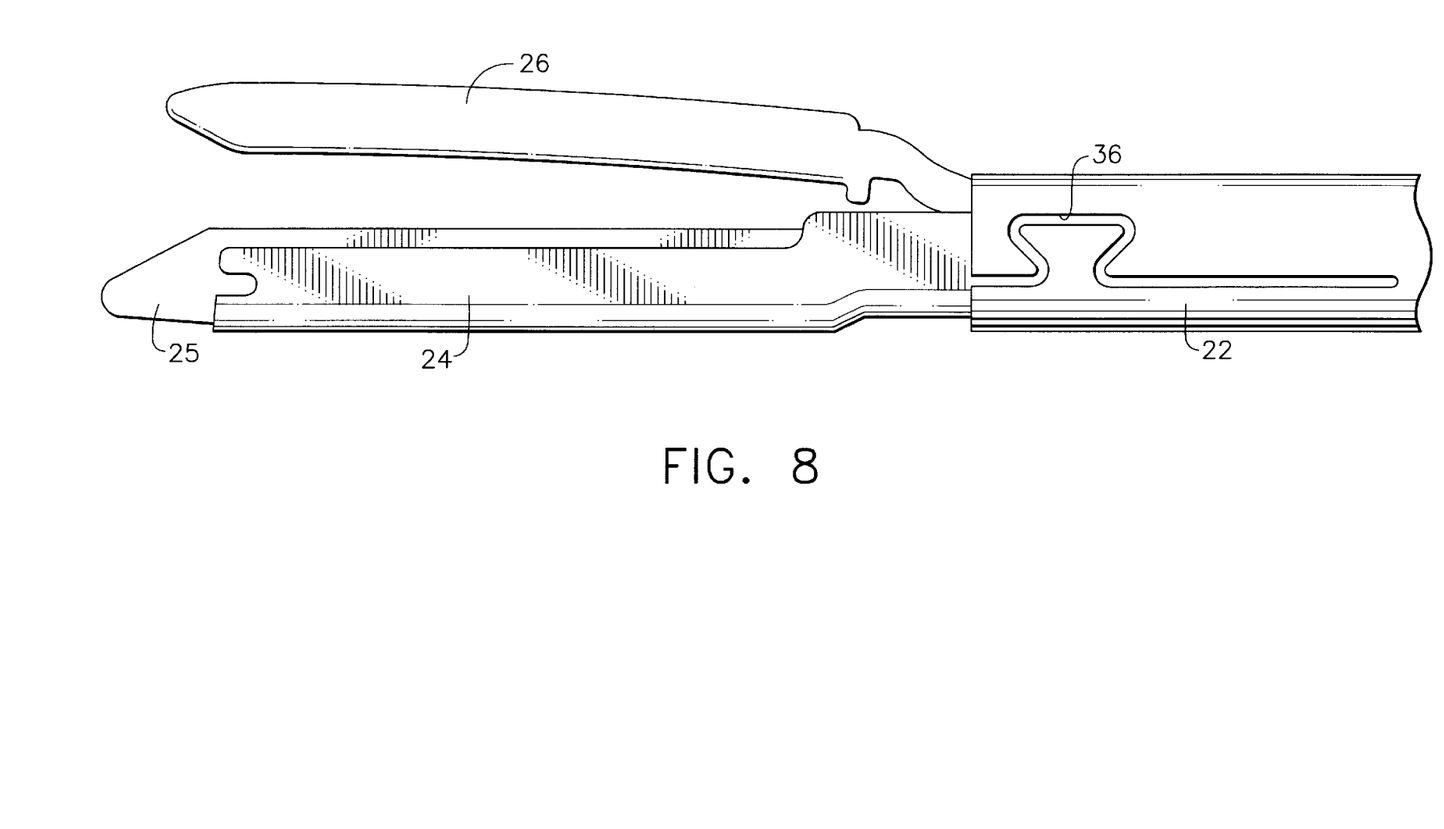
FIG. 8 is a fragmentary side elevation view of yet another alternative embodiment of the end effector.

The alternative embodiments of FIG. 6–8 illustrate different ways in which the distal end of the closure sleeve can be made to expand to allow for the tissue-clamping gap 35 when tissue is clamped between the anvil and cartridge. As illustrated in FIG. 6, a serpentine slot 36 is provided on either one or both sides of the distal end of the closure sleeve 22. The incorporation of the slot enables the expansion of the distal end of the sleeve. When the sleeve expands, as depicted in FIG. 7, a plurality of "locking points" 37 firmly secure the distal end of the sleeve in its expanded condition for tissue clamping. The precise location of the locking points dictates the degree of expansion of the sleeve, and therefore the clamping force applied to the end effector when loaded with tissue. FIG. 8 as well illustrates a serpentine slot 36 displayed at the distal end of the closure sleeve.

Figure 9:
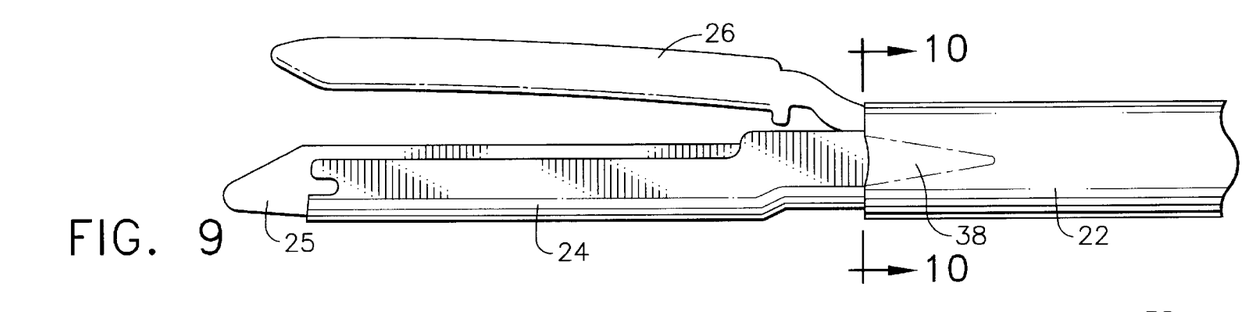
FIG. 9 is a fragmentary side elevation view of a further alternative embodiment of the end effector.
Figure 10:
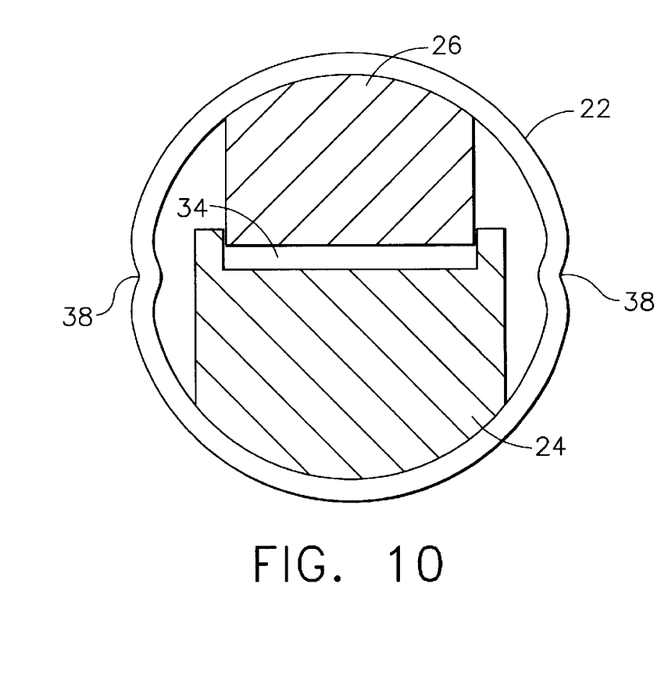
FIG. 10 is a section view generally taken along line 10—10 of FIG. 9.
Figure 11:
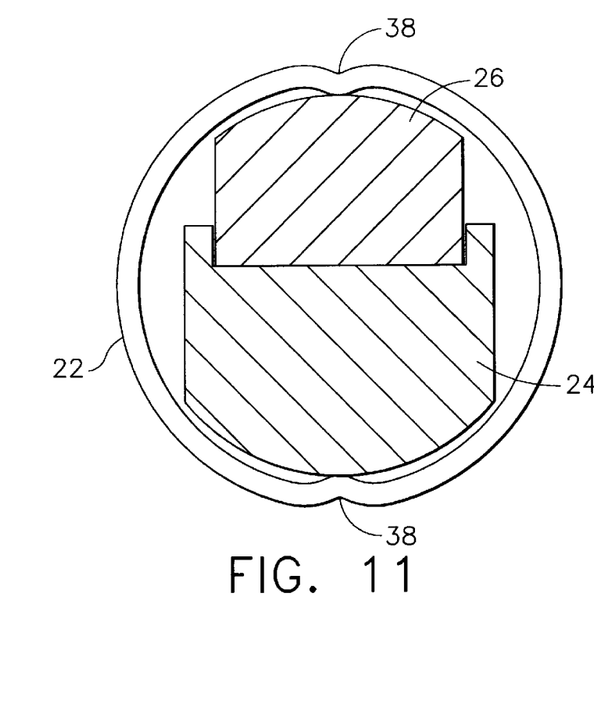
FIG. 11 is the section of FIG. 10 with the closure sleeve rotated 90° relative to the rotationally fixed components of the end effector.

Turning now to FIGS. 9–11, the closure sleeve 22 is used in combination with the anvil to provide movement of the anvil from a position allowing for the tissue-clamping gap 34 and another position where the tissue-clamping gap has been eliminated. The distal end of the rigid closure sleeve has a pair of swaged, mutually opposed indentations 38. The diameter of the sleeve is sized to accommodate the clearances for the cartridge-filled channel, anvil and tissue-clamping gap. When the closure sleeve is rotated 90° to position the swaged indentations into contact with the channel and anvil, the indentations urge the anvil to sit flush with the staple cartridge in the channel to eliminate the clearance provided by the tissue-clamping gap.

Figure 12:
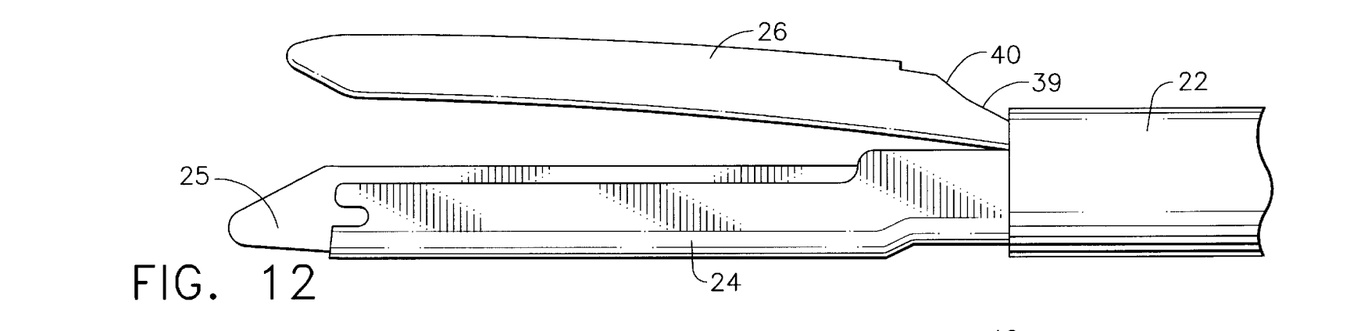
FIG. 12 is a fragmentary side elevation view of another alternative embodiment of the end effector where the anvil is in its second fixed position relative to the channel.
Figures 13, 14:
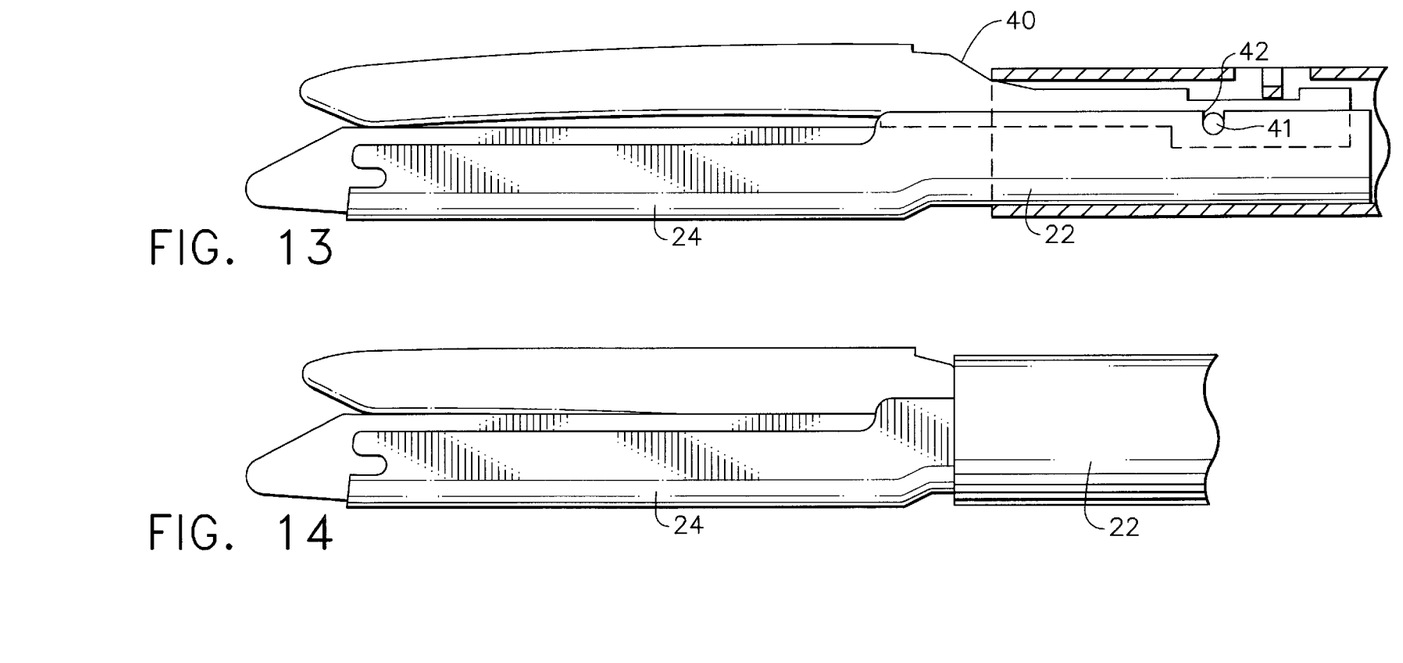
FIG. 13 is the end effector of FIG. 12 where the anvil is in its third fixed position relative to the channel.
FIG. 14 is the end effector of FIG. 12 where the anvil is in its first fixed position relative to the channel.

Referring to FIGS. 12–14, the closure sleeve is used in combination with a ramped, cambered anvil to provide the mechanism for moving the anvil into the three desired fixed positions relative to the channel of the end effector. "Camber" refers to the bend or bow in the anvil to allow its distal end to initially contact the cartridge prior to the remaining portion of the anvil to preload the anvil during closure. The anvil has a first proximal ramped surface 39 immediately adjacent the distal end of the closure sleeve when the closure sleeve is in its rearward position. Extending from the first ramped surface is a second ramped surface 40. The second ramped surface is steeper than the first ramped surface. The proximal end of the anvil is fixed to an anvil pivot pin 41, and the pin sits in a retention slot 42 in the channel. When the closure sleeve moves from its rearward position forwardly to an intermediate position as illustrated in FIG. 13, the anvil correspondingly moves downwardly from a position spaced from the cartridge to a position adjacent to the cartridge where a clearance between the two components is maintained for proper tissue clamping. When the closure tube is further moved forwardly from its intermediate position to its forwardmost position as depicted in FIG. 14, it slides on the second ramped surface and applies further downward pressure against the anvil to eliminate the clearance.

Figure 15:
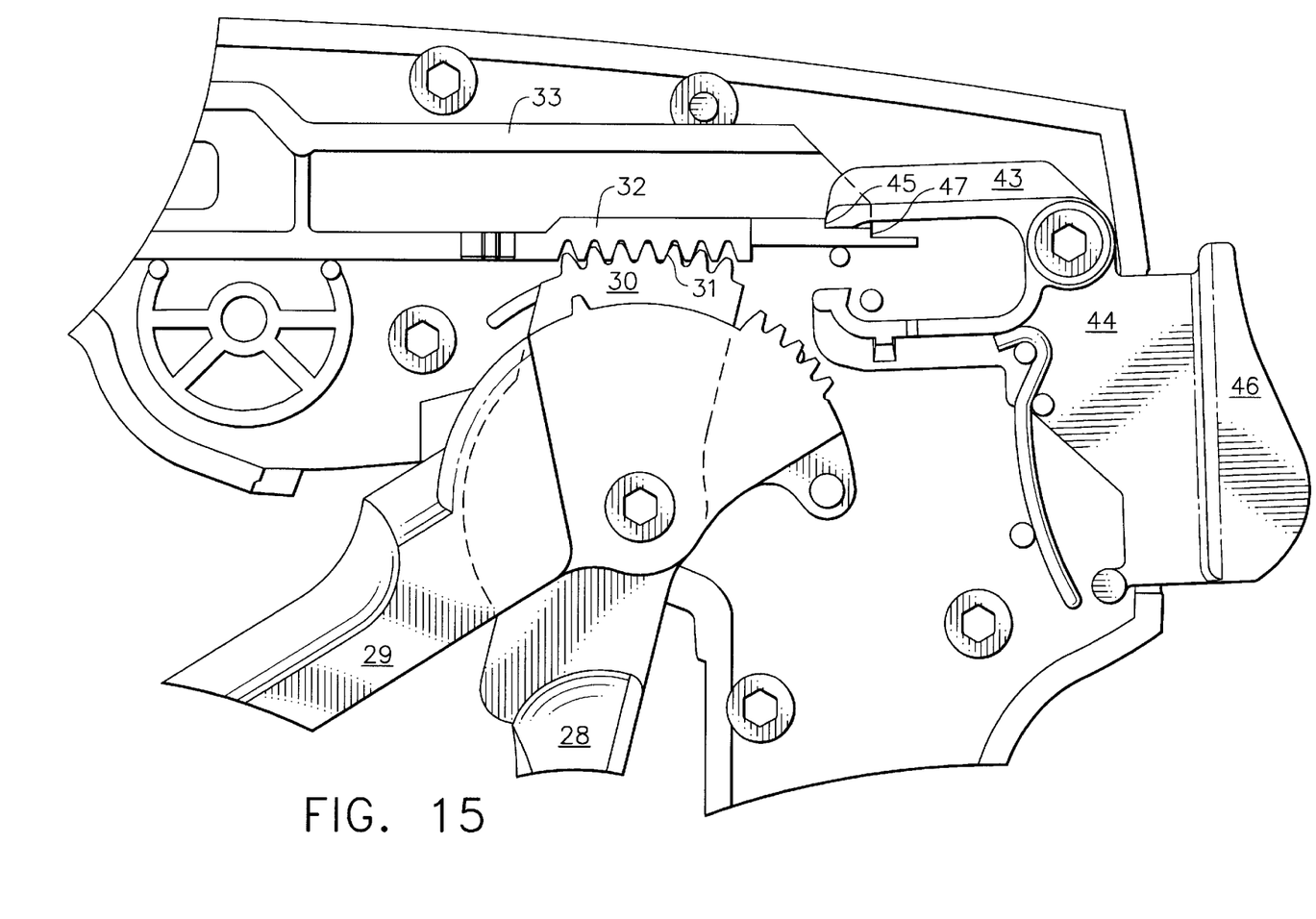
FIG. 15 is a fragmentary side elevation of the components inside the frame subassembly which enable actuation of the end effector depicted in FIGS. 12–14.

Referring now to FIG. 15, as the clamping trigger 28 is initially squeezed to move the closure sleeve from its rearward position to its intermediate position as illustrated in FIGS. 12 and 13, the upper latch arm 43 of the latch assembly 44 in the frame will slide into a first detent 45. An audible and tactile setting can be provided in cooperation with the thumb release 46 of the latch assembly when the upper latch arm moves into the first detent position to enable the user to know that the anvil is positioned relative to the cartridge in the manner depicted in FIG. 13. As the clamping trigger is further squeezed, the upper latch arm will move onto the second detent 47. Again, an audible <u>and tactile</u> setting can be provided to inform the user that he has positioned the anvil flush with the cartridge to eliminate the clearance between the cartridge and anvil as depicted in FIG. 14.

Figure 16:
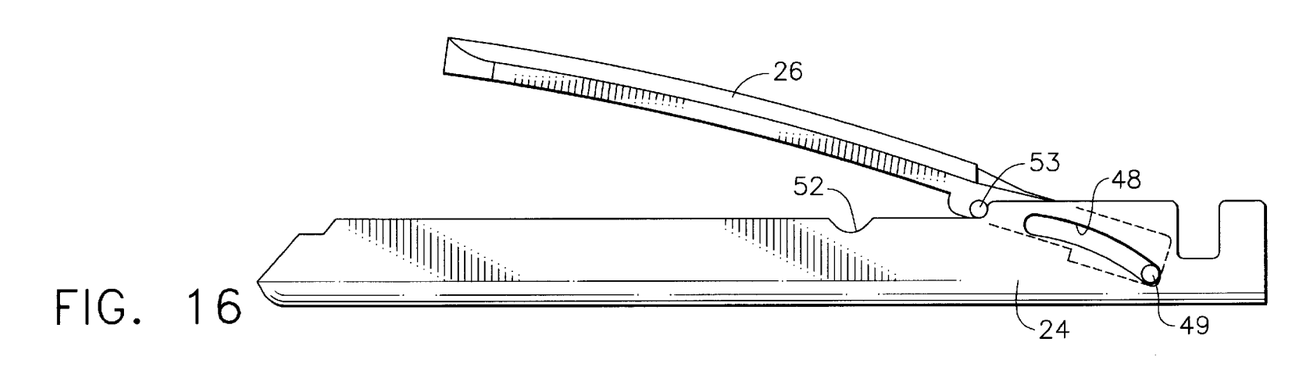
FIG. 16 is a side elevation view of the improved mechanism for moving the anvil from its second to third positions, which is described in commonly assigned, pending application Ser. No. 08/530,931, filed Sept. 19, 1995.
Figure 17:
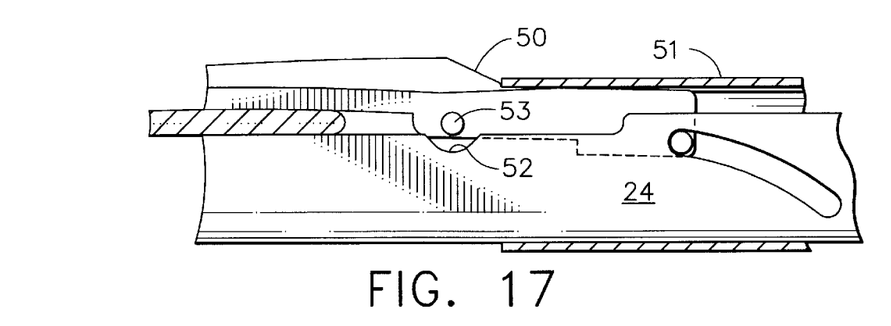
FIG. 17 is a fragmentary side elevation view of a modification of the end effector depicted in FIG. 16 which enables the anvil to move from its third to first fixed positions.
Figure 18:
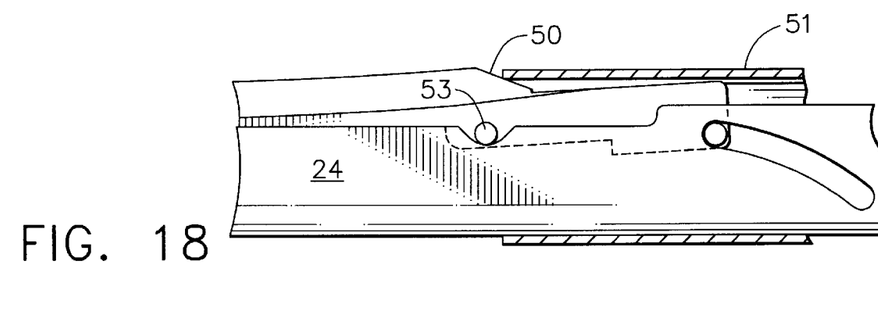
FIG. 18 is a fragmentary side elevation view illustrating the modified end effector depicted in FIG. 17 where the anvil is in its first fixed position relative to the channel.

Lastly, FIG. 16, in combination with FIGS. 17 and 18, provides another alternative embodiment for adjusting the movement of the anvil to provide three fixed positions relative to the channel of the end effector. As illustrated in FIG. 16, the channel may contain a generally diagonal slot 48 for movement of a slot post 49 which is affixed to the anvil 26. As the slot post rides up and down within the channel slot, the anvil correspondingly moves toward and away from the channel. A detailed description of this closure mechanism is provided in commonly assigned, copending application Serial No. 08/530,931, filed Sep. 19, 1995. The modification which enables the positioning of the anvil to substantially eliminate the conventional clearance between the cartridge and anvil is shown in FIGS. 17 and 18. Specifically, the anvil is provided with a ramped surface 50, and a closure member 51 is provided to slide on the ramped surface. When the slot post affixed to the anvil has ridden to its forwardmost position to position the anvil adjacent the cartridge, the closure member slides on the ramped surface. Consequently, the anvil is further urged forwardly to eliminate the tissue-clamping gap. Further facilitating the capability of the closure member to force the anvil flush against the staple cartridge, the channel is provided with a channel release 52 upon which an anvil slide pin 53 can rest to enable proper alignment of the entire anvil across the staple cartridge.

Although this invention has been described in connection with its most preferred embodiment, numerous additional embodiments are readily envisioned by those skilled in the art and therefore fall within the scope and spirit of the claimed invention. Accordingly, the preferred embodiments described in the specification are merely intended to be exemplary to provide a clearer understanding of the nature of the invention, and should not be construed in any way to limit the scope of the invention.

What is claimed is:

1. An endoscopic surgical stapler capable of clamping bodily tissue prior to firing staples to fasten said tissue, said stapler comprising:

an end effector including an anvil and an elongated channel containing a staple cartridge therein, said anvil facing said channel and movable toward and away therefrom, and said anvil having a first proximal ramped surface and a second ramped surface extending from said first ramped surface, said first and second surfaces having first and second slopes, respectively, said second slope being steeper than said first slope;

wherein said anvil is moveable to first, second and third fixed positions relative to said channel, said first fixed position being a closed position wherein said anvil is in intimate contact with said staple cartridge thereby eliminating any clearance therebetween, said second fixed position being an open position wherein said anvil is spaced from said cartridge for inserting said bodily tissue therebetween, and said third fixed position being a clamped position wherein said anvil is adjacent said cartridge so as to provide a tissue-clamping gap therebetween for clamping said bodily tissue.

2. The stapler of claim 1 further comprising a reciprocating closure sleeve from which said end effector extends, said sleeve being movable from a rearward position to an intermediate position wherein said sleeve slides on said first proximal ramped surface of said anvil so as to move said anvil from said second to third fixed positions, and said sleeve being movable from said intermediate position to a forward position wherein said sleeve slides on said second ramped surface so as to move said anvil from said third to first fixed positions.

* * * * *